United States Patent [19]

Kimura

[11] 4,402,310

[45] Sep. 6, 1983

[54] ENDOSCOPE SYSTEM

[75] Inventor: Tetsuya Kimura, Fuchu, Japan

[73] Assignee: Olympus Optical Co., Ltd., Tokyo, Japan

[21] Appl. No.: 206,374

[22] Filed: Nov. 13, 1980

[30] Foreign Application Priority Data

Nov. 22, 1979 [JP] Japan .................................. 54/151611

[51] Int. Cl.³ .............................................. A61B 1/06
[52] U.S. Cl. ........................................... 128/4; 128/6; 604/30; 604/35; 604/36
[58] Field of Search ................................. 128/4–11, 128/3, 214 R, 348, 349 R, 276, 273, 278; 604/22, 27, 30, 35–36, 45, 173, 246

[56] References Cited

U.S. PATENT DOCUMENTS

| 2,855,672 | 10/1968 | Franwick et al. ....................... 32/28 |
| 3,494,363 | 2/1970 | Jackson ........................... 128/303.14 |
| 3,517,669 | 6/1970 | Buono et al. .......................... 128/276 |
| 3,565,076 | 2/1971 | Kadan ................................... 128/278 |
| 3,726,272 | 4/1973 | Fukami et al. ........................... 128/6 |
| 3,730,645 | 5/1973 | Mashakaru et al. ............. 128/278 X |
| 4,094,318 | 6/1978 | Burke et al. .................... 128/214 E |
| 4,261,343 | 4/1981 | Ouchi et al. ............................. 128/4 |
| 4,270,525 | 6/1981 | Furihata ................................. 128/4 |
| 4,311,134 | 1/1982 | Mitsui et al. ............................ 128/6 |

FOREIGN PATENT DOCUMENTS

| 24706 | 11/1981 | European Pat. Off. . |
| 2912303 | 10/1979 | Fed. Rep. of Germany .......... 128/4 |

Primary Examiner—Lee S. Cohen
Assistant Examiner—Angela D. Sykes
Attorney, Agent, or Firm—Frishauf, Holtz, Goodman & Woodward

[57] ABSTRACT

An endoscope system comprises an endoscope provided with passages through which air and water are supplied and sucked and pumps for conducting air and water through the corresponding passages. The control section of the endoscope is provided with switches for generating electrical signals to freely preset the flow rates of air and water. Tubes for connecting pumps to the air passages are provided with valves for controlling the flow rates of air and water. The valves are opened by a servo motor driven by a servo motor drive circuit in accordance with the signal levers of the electrical signals issued from the switches.

16 Claims, 5 Drawing Figures 4,402,310

ENDOSCOPE SYSTEM

BACKGROUND OF THE INVENTION

This invention relates to an endoscope system, and more particularly to an endoscope which is provided with means for adjusting a flow rate of a fluid supplied to a distal end of the endoscope or drawn off therefrom through its internal fluid passage.

Some endoscope systems comprise internal fluid passages for supplying or drawing off air and water and also a device for supplying or drawing off air and water through said fluid passages. With the above-mentioned type of endoscope system, it is preferred to adjust an amount of a fluid supplied or drawn off in accordance with the physiological condition of that portion of a coeliac cavity of, for example, a human body (hereinafter simply referred to as "the coeliac cavity") which is to be observed through the endoscope. A flow rate-adjusting device known to date is a mechanically adjustable valve. The conventional endoscope system comprises said mechanically adjustable valve which is provided in the control section of the endoscope to adjust a flow rate of a fluid running through the fluid passage. The control section provided with the mechanically adjustable valve undesirably has an increased weight and large size, giving rise to difficulties in operating and handling the control section. The control section of the prior art endoscope is provided with switches for actuating pumps for supplying and drawing off air and water, and enables an amount of a fluid conducted through any of the various fluid passages to be adjusted by intermittently actuating the selected one of the switches. However, a fluid flow rate-adjusting device proposed to date is still regarded as unadaptable for practical application, because a minute adjustment of a fluid flow rate is difficult, and the repeated operation of the switches involves complicated work.

It is accordingly an object of this invention to provide an endoscope system whose control section can minutely adjust a flow rate of a fluid running through the internal fluid passage, and is reduced in weight and size, thereby enabling the endoscope system to be easily operated.

SUMMARY OF THE INVENTION

To attain the above-mentioned object, this invention provides an endoscope system which comprises:

an endoscope provided with at least one fluid passage allowing for the run of a fluid;

means provided in the endoscope to generate a signal for presetting the flow rate at which a fluid is to be conducted through the fluid passage; and means, which, upon receipt of said signal, causes a fluid to run through the fluid passage at the preset flow rate.

This invention can be more fully understood from the following detailed description when taken in conjunction with the accompanying drawings.

DETAILED DESCRIPTION

Figure 1:
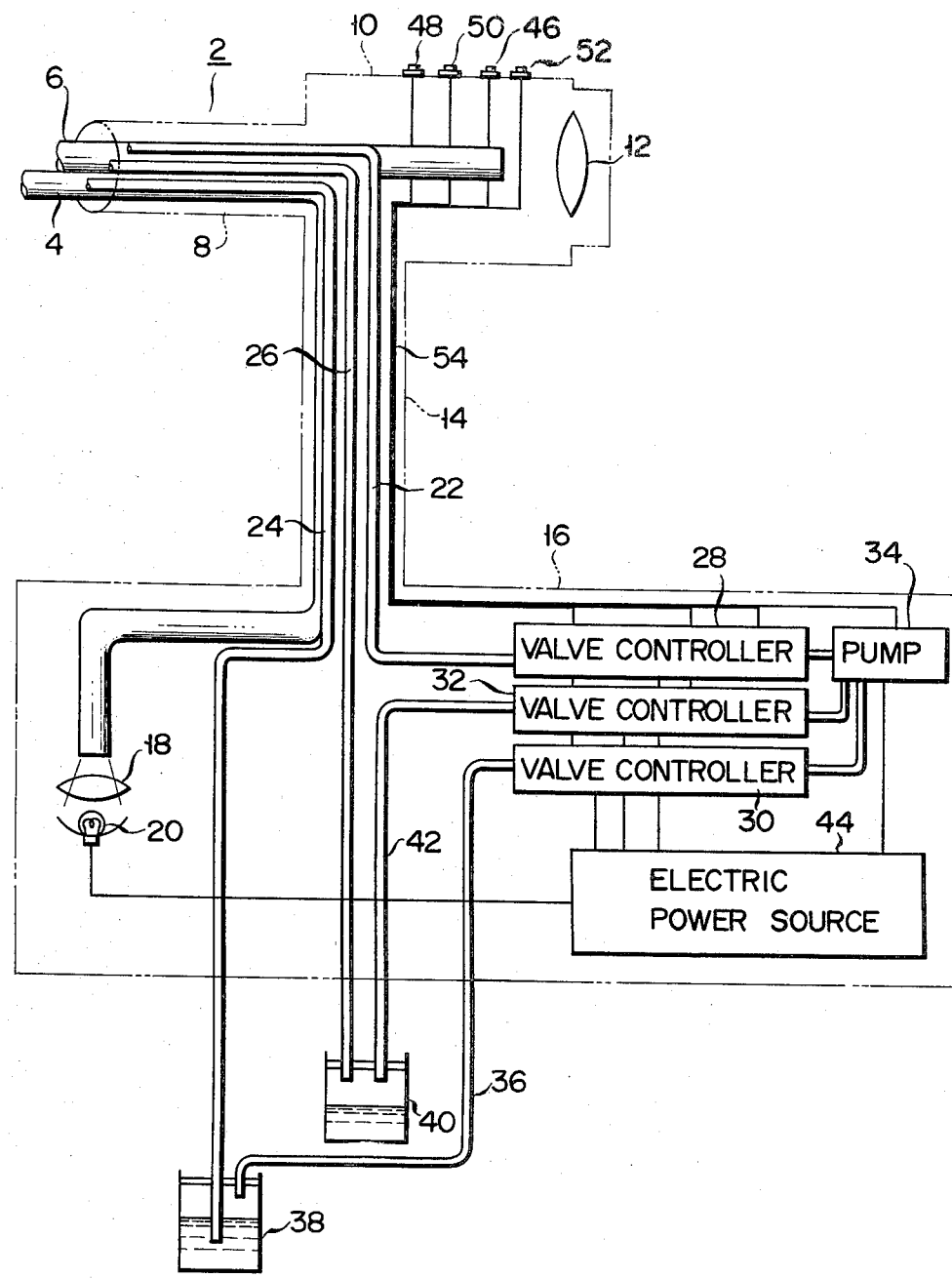
FIG. 1 schematically shows the arrangement of an endoscope according to one embodiment of this invention.

Referring to FIG. 1, schematically showing an endoscope system according to one embodiment of this invention, an endoscope 2 comprises, as is known, a light guide 4 and image guide 6. The image guide 6 extends from the distal end (not shown) of the endoscope to the front side of an eyepiece 12 of a control section 10 through an insertion section 8 to be put into the coeliac cavity. The light guide 4 extends from the distal end (not shown) of the endoscope to a light source unit 16 through the insertion section 8, control section for operating and handling the endoscope 2 and universal cord 14. The light guide 4 faces a focusing lens 18 in the light source unit 16 to receive light beams sent forth from a light source 20. An air supply tube 22, a tube 24 for supplying water or a physiological salt solution (hereinafter simply referred to as "water") and suction tube 26 extend through the insertion section 8 to the distal end of the insertion section 8. The air supply tube 22 and water supply tube 24 communicate at one end with an ejection port formed in a distal end face of the insertion section 8. The suction tube 26 communicates at one end with an ejection port formed at the distal end face of the insertion section 8. The ejection port faces an observation window. Water or air is forcefully thrown through the ejection port on to an objective lens to wash and clean it. The air supply tube 22, water supply tube 24 and suction tube 26 extend at the other end out of the endoscope 2 through the universal cord 14 into, for example, the light source unit 16. The light source unit 16 contains a pump 34 and valve controllers 28, 30, 32 for controlling the flow rate of water. The air supply tube 22 is coupled to the pump 34 through the valve controller 28 for adjusting the flow rate of air running through said air supply tube 22. The water supply tube 24 extends to the bottom of a tank 28 for holding the water which is to be conducted through the water supply tube 24. The water tank 38 is sealed in an airtight state. An air supply tube 36 for applying pressure to the water of the water tank 38 for the withdrawal of said water extends to the upper part of the water tank 38. Said air supply tube 36 is coupled to the pump 34 through the valve controller 30. The suction tube 26 communicates with a contaminated liquid tank 40 sealed in an airtight state to collect a sucked contaminated liquid. A suction tube 42 communicates with the contaminated liquid tank 40 to hold the contents at negative pressure. The suction tube 42 is coupled to a pump 34 through the valve controller 32 for adjusting an amount of air sucked through the suction tube 42. The valve controllers 28, 30, 32, pump 34 and light source 20 are connected to an electric power source 44. The control section 10 is provided with control switches 46, 48, 50 respectively used for air supply, water supply and suction, and also with a pump switch 52. These switches 46, 48, 50, 52 are electrically connected to the valve controllers 28, 30, 32 and pump 34 through signal lines 54 extending through the universal cord 14.

Figure 2:
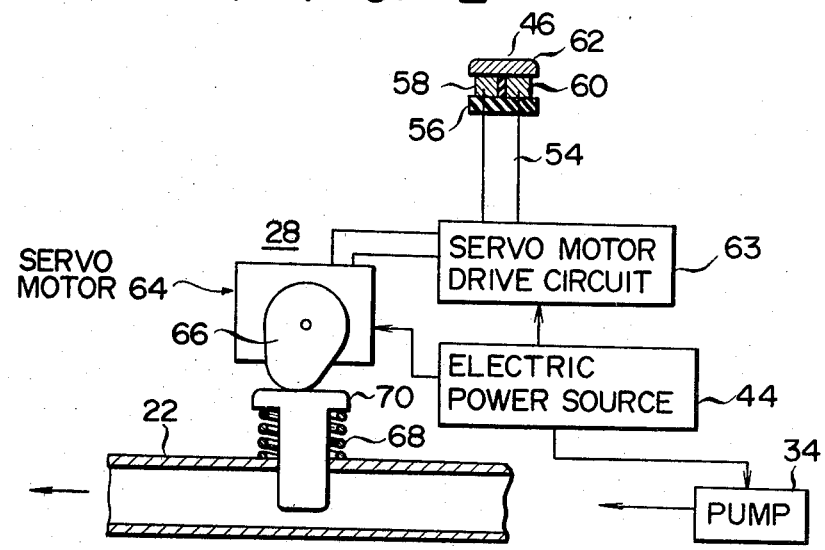
FIG. 2 schematically indicates the arrangement of an assembly of an air supply switch and valve controllers of FIG. 1.

The air supply valve controller 28 and air supply switch 46 for supplying said controller 28 with an air flow rate-instructing signal are assembled as shown in FIG. 2. The air supply switch 46 comprises a pair of electrodes 58, 60 spatially mounted on an insulation substrate 56. A button 62 formed of pressure-sensitive and electrically conductive rubber covers the paired electrodes 58, 60, which in form are connected to each other by means of said button 62. As is well known, the pressure-sensitive and electrically conductive rubber is prepared by mixing silicone rubber with particles of electrically conductive metal or carbon, and has the property that the density of the particles of said rubber varies with the magnitude of an externally applied pressure with a resultant change in the resistance. Therefore, depression of the button 62 causes a resistance between the paired electrodes 58, 60 to change. These electrodes 58, 60 are connected to a servo motor drive circuit 63 of the air supply valve controller 28 through signal lines 54. The servo motor drive circuit 63 is connected to a servo motor 64, whose rotary shaft is coupled to a cam 66 by means of a gear mechanism (not shown). The air supply tube 22 is fitted, as indicated in FIG. 2, with an air flow rate control valve 70 urged by a spring 68. The valve 70 is pressed against a cam 66 in a vertically movable state.

The water supply switch 48 and suction switch 50 have the same construction as the air supply switch 46 of FIG. 2. The valve controllers 30, 32 of FIG. 2 have the same construction as those of FIG. 1, description thereof being omitted.

Where, with the above-mentioned embodiment, the pump switch 52 provided in the control section 10 is closed, then electric power is supplied to the valve controllers 28, 30, 32 and pump 34 from the power source 44. Though, at this time, the pump 34 is actuated, the valves 70 of the valve controllers 28, 30, 32 are so urged by the cam 66 to close the passages of the corresponding tubes 22, 36, 42. Therefore, air supply, water supply and suction are not carried out. Where the air supply switch 46 is depressed, then the resistance of the button 42 of this switch 46 decreases in accordance with the force of said depression, causing the servo motor drive circuit 63 to be operated. This servo motor drive circuit 63 causes the servo motor 64 to be rotated a number of times corresponding to the resistance of the button 62. As a result, the shaft of the cam 66 coupled to the rotary shaft of the servo motor 64 is rotated through a prescribed angle, causing the cam 66 to be rotated to the corresponding extent. At this time, the valve 70 is pushed upward by the spring 68 to a prescribed extent, causing the passage of the air supply tube 22 to be opened to a predetermined extent. Air is introduced into the coeliac cavity by the pump 34 through the air supply tube 22 at a preset flow rate. Where the air supply switch 46 is released from depression, then the button 62 again increases in resistance. Accordingly, the servo motor drive circuit 63 causes the servo motor 64 to be reversely driven, thereby bringing the rotary shaft of said motor 64 back to its original position. Accordingly, the cam 66 is reversely rotated to regain its original position, and pushes the valve downward to shut off the passage of the air supply tube 22. Where the water supply switch 48 and suction switch 50 are depressed, the flow rate of a fluid conducted through the tubes 36, 42 is also adjusted. In other words, the valve 70 has its position varied with the resistance of the button 62 defined by the magnitude of a force with which the switch 48 or 50 is depressed, resulting in a change in the cross sectional area of the fluid passage. Where a fluid runs through the tube 36 at a higher flow rate, then water is let to pass from the water tank 38 to the water supply tube 24 in a larger amount. Where air is sucked into the suction tube 42 in a large amount, air and water are supplied to the water tank 40 through the suction tube 42 in an increased amount.

With the embodiment of FIG. 2, the flow rate of air and water and the amount of these fluids to be sucked can be freely controlled by adjusting the force with which the switches 48, 50, 52 provided in the control section 10 of the endoscope 2 are depressed.

Figure 3:
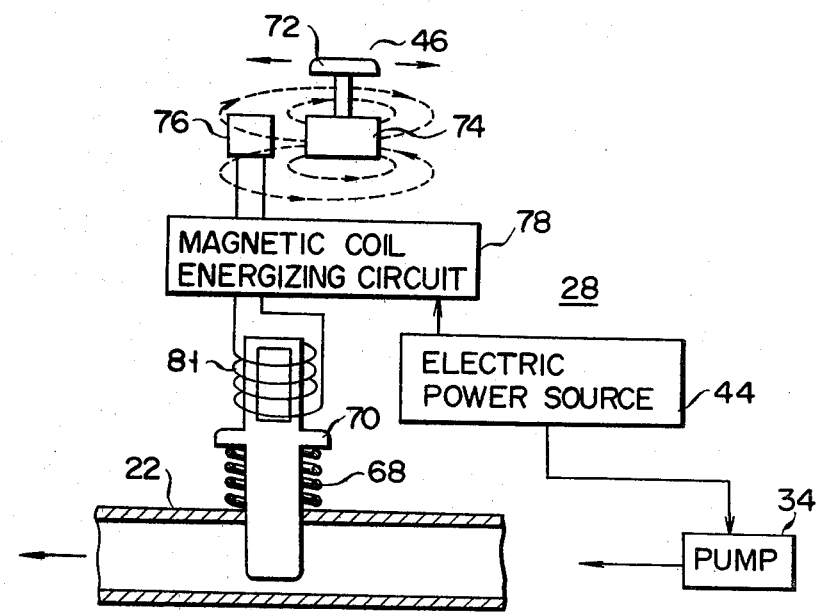
FIG. 3 schematically shows the arrangement of another assembly of an air supply switch and valve controllers of FIG. 1.

FIG. 3 shows an air supply switch 46 and valve controller 28 modified from those of FIG. 1. The water supply switch 48 and suction switch 50 are constructed as shown in FIG. 3. The air supply switch 46 is provided in the control section 10 in a state slidable along its surface. A permanent magnet 74 is supported by the button 72 of the air supply switch 46 in a state slidable through the control section 10. A magnetic resistor 76 prepared from, for example, InSb or NiSb is set on a line along which the permanent magnet 74 slides. The internal resistance of said magnetic resistor 76 varies with the intensity of a magnetic field penetrating through said permanent magnet 74. The magnetic resistor 76 is connected to a magnetic coil-energizing circuit 78 which is supplied with electric power from the electric power source 44. The magnetic coil-energizing circuit 78 is connected to a magnetic coil 80 which magnetically pushes a permanent magnet piece provided on the valve 70 downward against the urging force of the spring 68.

When, with the embodiment of FIG. 3, the pump switch 52 is closed, then electric power is supplied from the electric power source 44 to the pump 34 and magnetic coil-energizing circuit 78 for their actuation. When the permanent magnet 74 of the switch 46 is removed from the magnetic resistor 76, then a weak magnetic field is generated in said magnetic resistor 76, which in turn indicates a fully weak resistance. At this time, the magnetic coil-energizing circuit 78 supplies a sufficient current to the magnetic coil 80. Magnetic force generated in the magnetic coil 80 magnetically acts on the permanent magnet piece 81 provided on the valve 70 to magnetically push the valve 70 and close the passage of the air supply tube 22. When approached by the permanent magnet 74 of the switch 46, the magnetic resistor 76 increases in resistance. At this time, the magnetic coil-energizing circuit 78 supplies a small current to the magnetic coil 80, which in turn sends forth a decreased magnetic force to the valve 70. As a result, the valve 70 is lifted to open the passage of the air supply tube 22.

With the embodiment of FIG. 3, the slide of the switch 46 allows for the free adjustment of the flow rate of air conducted through the tube 22. The magnetic resistor 76 may be replaced by a Hall-effect element.

Figure 4:
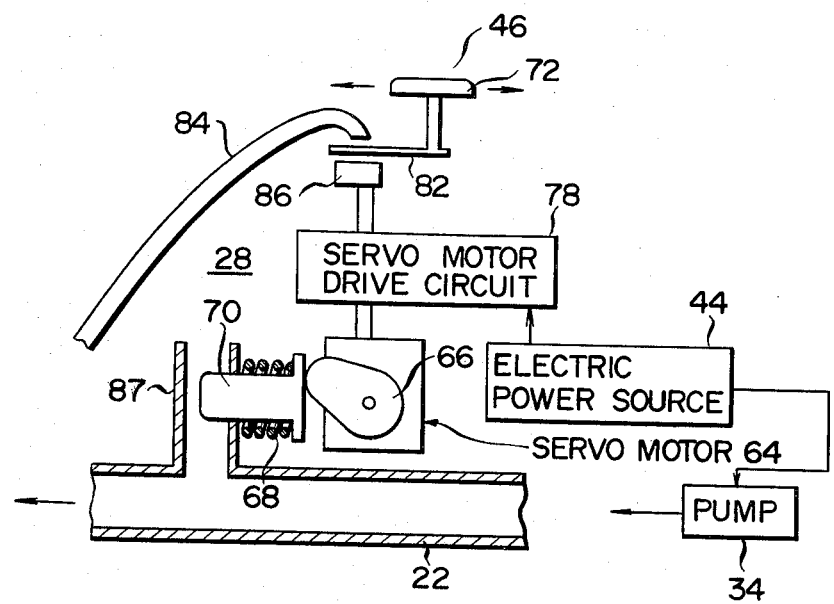
FIG. 4 schematically illustrates the arrangement of still another assembly of an air supply switch and valve controls of FIG. 1.

Description is now given of an endoscope system of FIG. 4 according to still another embodiment of this invention. As in FIG. 3, the switch 46 is slidably provided in the control section 10. A light-obstructing plate 82 is supported by the button 72 of the switch 46. This plate 82 is made to slide through the control section 10 to a minute extent. The light-obstructing plate 82 extends from the light source unit 16 and is made to slide through a space defined between the end face of the additional light guide 84 receiving a light from the light source unit 16 and a light-detecting element 86 facing said light guide 84. The light-detecting element 86 is connected to the servo motor drive circuit 63, which in turn is connected to the electric power source 44 and servo motor 64. The cam 66 is coupled to the rotary shaft of the servo motor 64 through a gear mechanism. The cam 66 is pressed against the valve 70 urged by the spring 68, in such a manner that said valve 70 can slide against the urging force of the spring 68. With the embodiment of FIG. 4, said valve 70 is provided in an air tube 87 communicating with the air supply tube 22.

When, with the embodiment of FIG. 4, the button 72 of the switch 46 is depressed, then the light-obstructing plate 82 has its position varied, giving rise to a change in an amount of a light emitted through the light guide 84 to the light-detecting element 86. As in FIG. 1, the servo motor drive circuit 63 rotates the servo motor 64 a number of times corresponding to the resistance of the light-detecting element 86, causing the cam 66 to be rotated through the corresponding angle. As a result, the valve 70 is moved against the urging force of the spring 68 to open the air tube 87 by a prescribed cross sectional area. Consequently, the negative pressure of air conducted through the tube 22 by the pump 34 drops, decreasing the flow rate of air running through the tube 22. Thus, the flow rate of air in the tube 22 can be adjusted by the movement of the switch 46.

Figure 5:
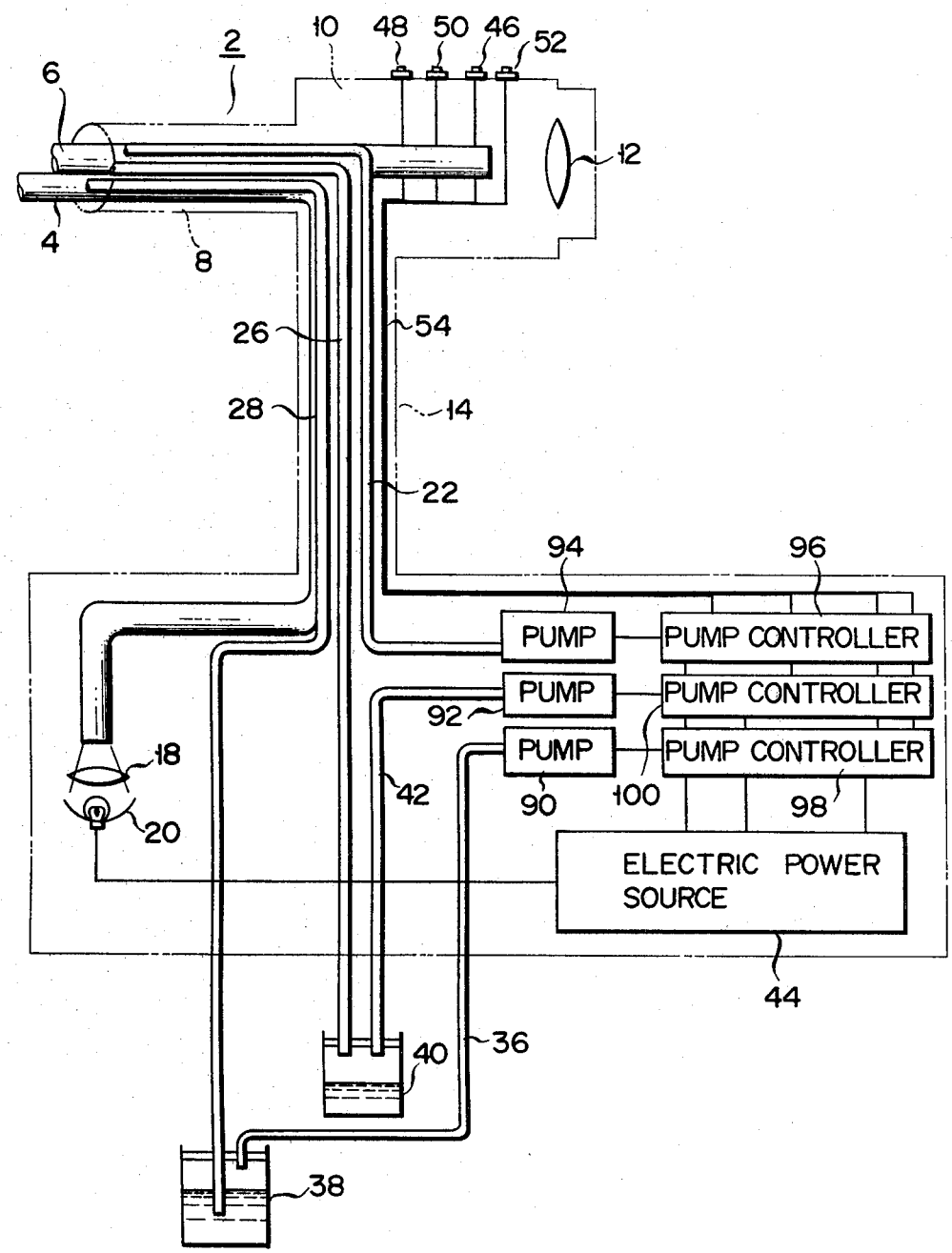
FIG. 5 schematically shows the arrangement of an endoscope system according to another embodiment of the invention.

Description is now given of an endoscope system of FIG. 5 according to a further embodiment of this invention. The parts of FIG. 5 the same as those of the other embodiments are denoted by the same numerals, description thereof being omitted. Unlike the embodiment of FIG. 1, the embodiment of FIG. 5 comprises pumps 90, 92, 94 respectively provided for the tubes 22, 36, 42. These pumps 90, 92, 94 are respectively connected to pump controllers 96, 98, 100 which control electric power supplied from the electric power source 44 to said pumps 90, 92, 94 to adjust their number of rotations. The pump switch 52 is connected between the pump controllers 96, 100, 98 and electric power source 44. The air supply switch 46 is connected to the air supply pump controller 96; the water supply switch 48 to the water supply pump controller 98; and the suction switch 50 to the suction pump controller 100. These switches may be of any of the types described with reference to FIGS. 3 to 5 or of the type formed of a plurality of variable or stepwise variable resistors. In short, the switches 46, 48, 50 are preferred to be of such type that the pump controllers 96, 98, 100 can control an amount of electric power supplied to the corresponding pumps 88, 90, 92 in accordance with the operating conditions of said switches 46, 48, 50, in order to adjust the number of rotations of said pumps 88, 90, 92.

When, with the embodiment of FIG. 5, any of the switches 46, 48, 50 is made to slide or is depressed, then the corresponding one of the pumps 88, 92, 90 is rotated a prescribed number of times, thereby adjusting the flow rate of a fluid conducted through a tube by any of the pumps 88, 92, 90.

With an endoscope system embodying this invention, a switch provided in the control section of the endoscope minutely adjusts the flow rate of air or water conducted through a tube, thereby making it possible to supply such air or water at an optimum rate for the physiological condition of that part of the coeliac cavity which is observed by an endoscope. For example, when the blood continues to run out vigorously in a large amount, or is already considerably connected in that defective part of the coeliac cavity which is being observed by the operator, then the endoscope system of this invention can quickly suck out the blood by accelerating the suction rate. Further, where the soiled observation window at the distal end of the insertion section of the endoscope is cleaned with water, and it is desired to pneumatically blow off water particles remaining on the surface of the observation window, then this object can be attained by accelerating the flow rate of compressed air.

When it is desired to pneumatically expand that part of the coeliac cavity which is to be observed, then the endoscope system of this invention decelerates the flow rate of air. This arrangement suppresses the rapid expansion of a defective coeliac part requiring observation which might occur by the otherwise accelerated flow rate of air, thereby saving said defective coeliac part from unnecessary pairs. Further, when only a small amount of blood or fluid remains in an observed defective coeliac part, then the endoscope system of the invention causes the blood or fluid to be sucked at a properly reduced rate. This arrangement is devised to avoid the possibility that if a small amount of blood or fluid is rapidly sucked, then the related coeliac wall will also be forcefully sucked or pulled as a result of said quick suction, and if, in this case, the vigorously sucked coeliac wall is weak, then the blood vessel of said wall will be broken, giving rise to fresh bleeding.

The endoscope system of the present invention has further advantages that the operation of the endoscope is controlled by switches provided in the control section, enabling the operator to apply only a small physical force; and the proximal end control section is simply provided with switches and, consequently, can be saved from a noticeable increase in weight.

What is claimed is:
1. An endoscope system comprising:
   an endoscope provided with an insertion section to be introduced into a coeliac cavity of a body, a control section remote from said insertion section for controlling the operation of the endoscope and a first fluid passage for supplying a fluid to said insertion section;
   signal generating means in said control section and including a first depressible electrical switching element provided on said control section for generating a first electrical signal having a signal level which is a function of a depression force applied to the first switching element;
   air flow generating means separate from said control section for generating an air flow;
   a first tube coupled to said air flow generating means and through which air flows, said first tube extending from the endoscope and communicating with the first fluid passage of the endoscope;
   a first valve coupled to said first tube for adjusting the flow rate of air flowing through the first tube, said first valve being located separate from said control section; and
   actuating means located separate from said control section and being coupled to said signal generating means and responsive to said first electrical signal for actuating said first valve for setting the flow of air through said first tube in accordance with the signal level of said first electrical signal from said signal generating means of said control section.

2. The endoscope system of claim 1, wherein said first depressible electrical switching element has an internal resistance which varies with the depression force applied to said first switching element.

3. The endoscope system of claim 1, wherein said signal generating means comprises:
- a permanent magnet slidably provided in the endoscope and being slidable along a line; and
- a magnetic resistor set on said line along which said permanent magnet is slidable.

4. The endoscope system of claim 1, wherein said signal generating means comprises:
- a light guide through which a light is conducted, said light guide having a light-projecting end face;
- a light-detecting element set opposite to said light-projecting end face of said light guide; and
- a slidable shielding plate disposed between said light guide and said light-detecting element and arranged to vary an amount of a light supplied to said light detecting element.

5. The endoscope system of claim 1, wherein said actuating means comprises:
- a motor for driving said first valve; and
- means for supplying said motor with a sufficient amount of power to allow said motor to rotate by a prescribed number of times corresponding to the signal level of said first electrical signal from said signal generating means.

6. The endoscope system of claim 5, wherein said motor is a servo motor.

7. The endoscope system of claim 1, wherein said valve actuating means comprises:
- a permanent magnet member mounted on said first valve;
- a magnet coil for applying a magnetic force to said first valve for its actuation; and
- a magnetic coil-energizing circuit for supplying said magnetic coil with electric power as a function of the signal level of said first electrical signal.

8. The endoscope system of claim 1, wherein:
- said means for generating an air flow includes a pump coupled to said first tube; and
- means is provided for rotating said pump a number of times corresponding to the signal level of said first electrical signal.

9. The endoscope system of claim 1, wherein said fluid is air; and said first fluid passage of the endoscope is an air passage through which the air flows.

10. The endoscope system of claim 1, wherein:
- a tank is provided for containing water, said tank being coupled to said first tube;
- said fluid is water; and
- water is supplied from said tank to a coeliac cavity of a body through said first fluid passage of the endoscope.

11. The endoscope system of claim 1, wherein:
- a tank is provided and is coupled to said first tube;
- said fluid is air; and
- said first fluid passage of the endoscope is a suction passage for sucking air and water from a coeliac cavity of a body into said tank.

12. An endoscope system comprising:
- an endoscope provided with first, second and third fluid passages for supplying first, second and third fluids;
- signal generating means including first, second and third depressible switching elements provided on the endoscope for respectively generating first, second and third electrical signals which respectively have a signal level which is a function of a depression force applied to the corresponding switching element;
- means for generating an air flow;
- first, second and third tubes through which air flows and which extend from the endoscope and communicate with said first, second and third fluid passages of the endoscope, respectively;
- first, second and third valves coupled to said first, second and third tubes, respectively, for adjusting the flow rate of air flowing through said first, second and third tubes, respectively; and
- actuating means coupled to said signal generating means for actuating each of said first, second and third valves for setting the flow rate of air through said first, second and third tubes in accordance with the signal level of the corresponding electrical signal from said signal generating means.

13. The endoscope system of claim 12, wherein:
- the endoscope comprises an insertion section to be introduced into a coeliac cavity of a body, and a control section for controlling the endoscope; and
- said signal generating means is provided within said control section.

14. An endoscope system according to claim 12, wherein each of said first, second and third switching elements has an internal resistance which varies with the depression force applied to the respective switching element.

15. The endoscope system of claim 12, wherein said actuating means comprises:
- first, second and third motors for driving said first, second and third valves, respectively; and
- means for supplying power to each of said motors, said power being large enough to rotate the respective motor a prescribed number of times which corresponds to the signal level of the corresponding electrical signal from said signal generating means.

16. The endoscope system of claim 12, wherein:
- said first fluid is air;
- said first fluid passage of the endoscope supplies air;
- a first tank is provided for containing water, said second tube being coupled to said first tank;
- said second fluid is water;
- said second fluid paggage of the endoscope supplies water from said first tank to a coeliac cavity of a body;
- a second tank is provided, said third tube being coupled to said second tank;
- said third fluid is air and water; and
- said third fluid passage of the endoscope is a suction passage for sucking air and water from the coeliac cavity into said second tank.

* * * * *